United States Patent [19]
Watt

[11] Patent Number: 5,359,939
[45] Date of Patent: Nov. 1, 1994

[54] SUPPORT DEVICE FOR IN-LINE PIPE INSPECTION TOOL

[75] Inventor: Robert L. Watt, Friendswood, Tex.

[73] Assignee: Tuboscope Vetco International, Inc., Houston, Tex.

[21] Appl. No.: 77,435

[22] Filed: Jun. 17, 1993

[51] Int. Cl.⁵ .............................................. B61B 13/00
[52] U.S. Cl. .................................................... 104/138.2
[58] Field of Search ...................... 104/138.2, 138.1; 378/60; 358/100

[56] References Cited

U.S. PATENT DOCUMENTS 3,495,546  2/1970  Brown et al. ................... 104/138.2

FOREIGN PATENT DOCUMENTS 0163467  3/1989  Japan ............................. 104/138.2
0338463  2/1991  Japan ............................. 104/138.2
3153457  7/1991  Japan ............................. 104/138.2
1548098  3/1990  U.S.S.R. ......................... 104/138.2

*Primary Examiner*—Mark T. Le
*Attorney, Agent, or Firm*—Finnegan, Henderson, Farabow, Garrett & Dunner

[57] ABSTRACT

A device for the in-line inspection of pipe. The device is spring-loaded to provide an adequate pressure between the supporting brushes of the device and the interior pipe wall for effective magnetic inspection with pipe of various internal diameters. A biasing spring is used in association with the spring-loaded device to extend and provide a supplemental force when the device passes from a relatively small to a relatively large diameter pipe to rapidly and effectively position a magnetizing section of the device within the larger diameter pipe.

8 Claims, 7 Drawing Sheets

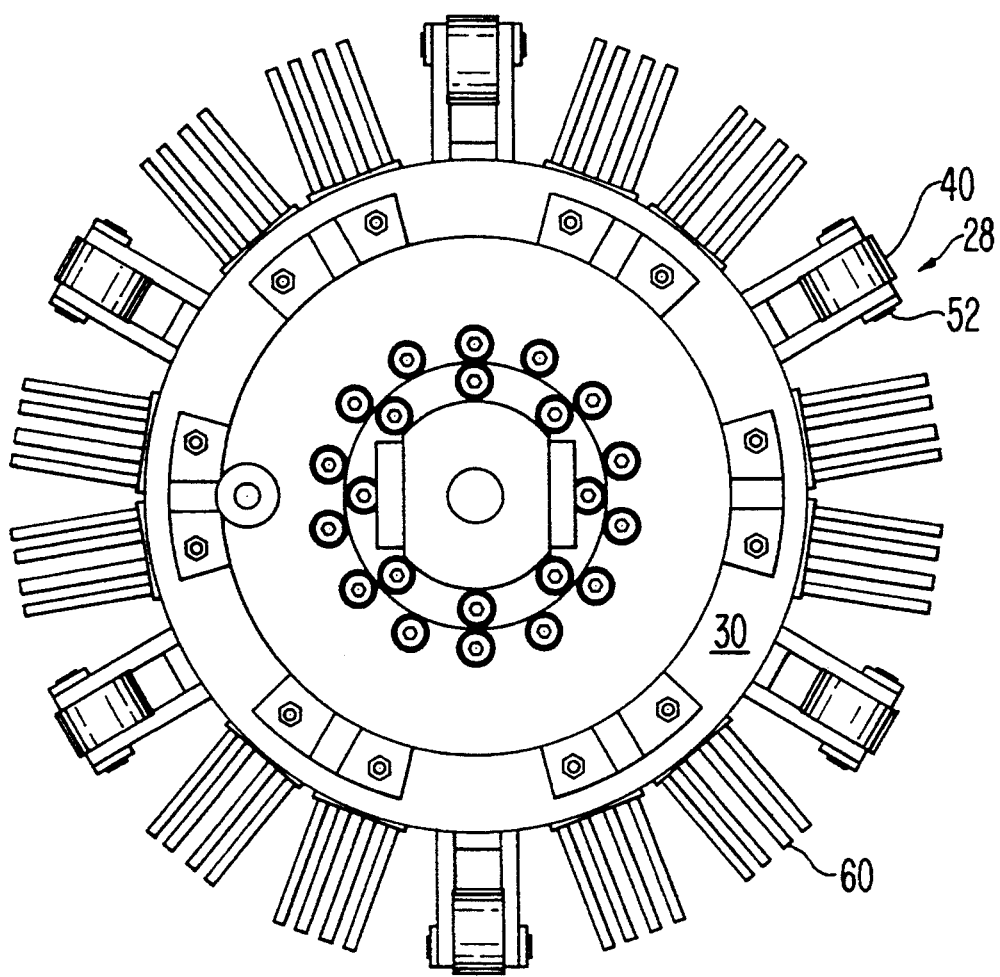

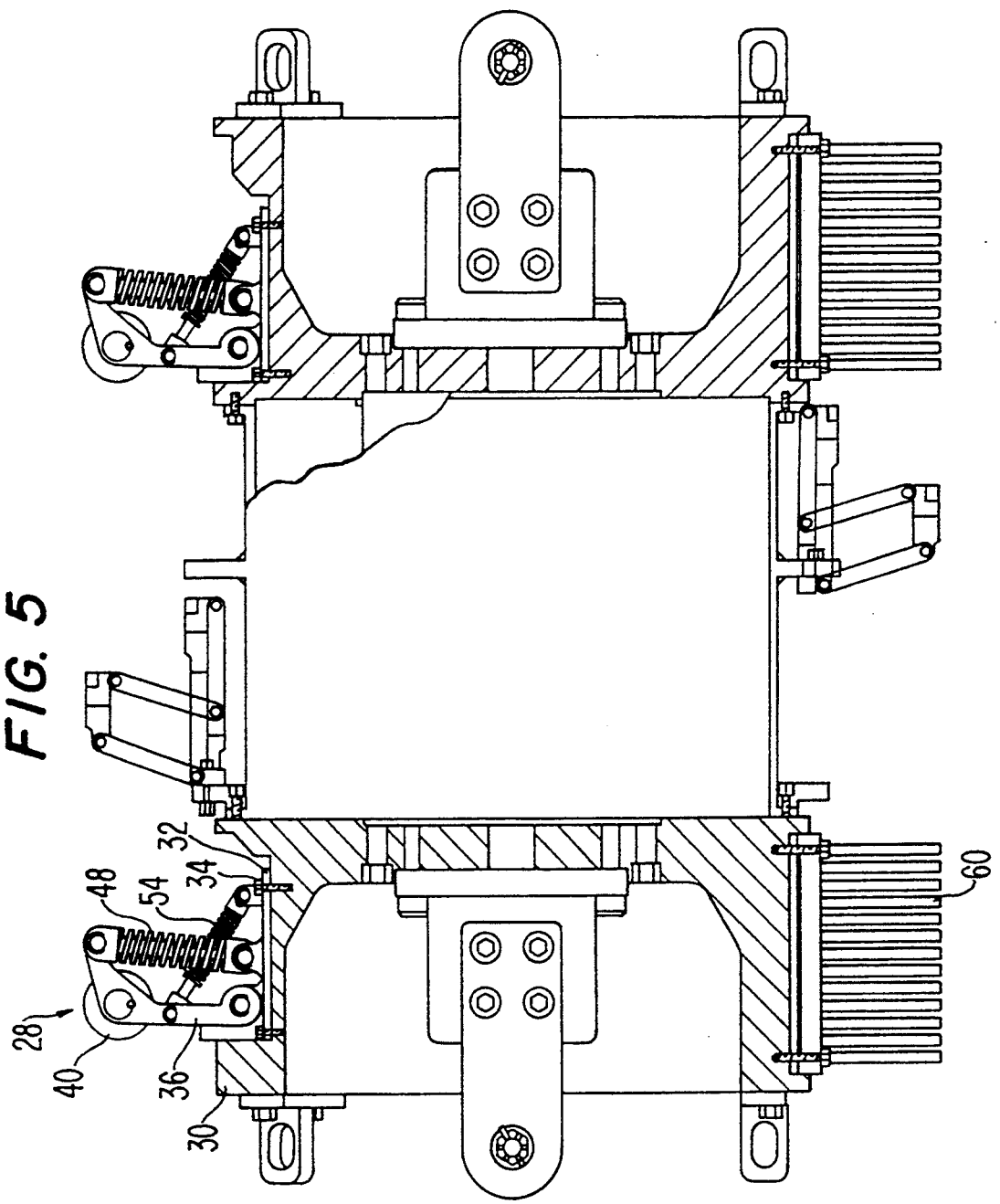

SUPPORT DEVICE FOR IN-LINE PIPE INSPECTION TOOL

BACKGROUND OF THE INVENTION

1. Field the Invention

The invention relates to a variable force support device for supporting an in-line pipe inspection tool during longitudinal travel of the tool through a pipe being inspected.

2. Description of the Prior Art

It is known to perform in-line inspection of pipe by magnetic flux leakage technology. With these inspection practices, an in-line pipe inspection tool is propelled through the pipeline by the flowing product therein, which for example may be oil. As the tool passes through the pipeline, a strong magnetic field is induced into the pipe wall. Defects in the form of discontinuities will cause redistribution of the magnetic flux around the defect. This results in some of the lines of magnetic flux leaking out into the surrounding medium. The inspection tool embodies an electromagnet which is battery powered to power an electromagnet that induces the magnetic flux field into the pipe wall. Two sets of steel brushes are used in conjunction with the electromagnet to constitute the magnetic north and south poles of the magnetic flux field. It is necessary to maintain constant contact between the two sets of brushes and the internal surface of the pipe to ensure an uninterrupted magnetic flux field within the pipe wall. This is difficult to achieve if a single inspection device is used with pipe of different diameters. A plurality of transducers are used to detect magnetic flux leakage indicating a defect in the pipe wall. The transducers provide a signal indicating the presence of a defect, which signal may be processed by various electronic recording arrangements.

The two sets of steel brushes employed with the magnetizer act to support the inspection tool during its travel through the pipe. After extended use of the inspection tool, these steel brushes tend to wear and deform as a result of the combination of the weight of the inspection tool being supported, the weight of the fluid in the pipe above the inspection tool and contact with the interior surfaces of the pipe. This results in misposition of the inspection tool during travel through the pipe and discontinuous contact between the steel brushes and the interior pipe wall surface. This adversely affects the desired uninterrupted magnetic flux field in the pipe wall necessary for effective defect detection. This condition is exacerbated when the tool is used with pipes of different diameters. With these applications the brushes are required to extend sufficiently to support the tool with increased diameter pipe and then compress when inspecting smaller diameter pipe. During extension of the brushes, there must be sufficient force exerted by the brushes against the pipe wall to provide the required contact to ensure an uninterrupted magnetic flux field within the pipe wall.

SUMMARY OF THE INVENTION

It is accordingly a primary object of the present invention to provide a support device that supports an in-line inspection tool during longitudinal travel of the tool through a pipe being inspected accurately and specifically centered within the interior of the pipeline, even in the presence of pipe of increased diameter, with the pressure between the brushes and the pipewall surface being adequate for effective inspection and relatively constant and uniform around the entire wall circumference.

A more specific object of the invention is to provide a force support device used in conjunction with the wire brushes for supporting the inspection tool, with the support device being adapted to provide adequate force between the pipe wall and the support device in the presence of increases in the internal diameter of the pipeline being inspected.

In accordance with the invention, a variable support device is provided for supporting an in-line pipe inspection tool during longitudinal travel of the tool through a pipe being inspected. The support device has rotating means, which may be a wheel, for rotational contact with an interior surface of the pipe during travel of the tool through the pipe. A spring arrangement, which may constitute a pair of coil springs parallel mounted on the support device at opposite ends of the wheel, is provided for applying force to the wheel to normally urge the wheel against the interior surface of the pipe and is adapted for compression in response to a compressive force transmitted thereto from the wheel resulting from contact of the wheel with the interior pipe surface. A second spring is provided to apply a supplemental biasing force to the wheel, with the supplemental biasing force increasing in relation to decreases in the force applied by the first spring arrangement to minimize force changes between the rotating wheel and the interior surface of the pipe. Means are provided for connecting the support device to the inspection tool.

The wheel is suitably journaled for rotation during longitudinal travel of the inspection tool through the pipe being inspected.

The second spring is bias mounted on the support device relative to the pair of coil springs.

The arrangement for connecting the support device to the inspection tool may include a base plate. A wheel support is connected to the base plate and extends therefrom at one end and at an opposite end has a bifurcated portion within which the wheel is journaled for rotation. An end of each of the pair of coil springs is connected to the bifurcated portion, and an opposite end of the springs is connected to the base plate. An end of the second spring is connected to the base plate and an opposite end of this spring is connected to the wheel support at a location thereon between the wheel and the base plate.

The inspection tool to which the support device is connected has a magnetizing portion that comprises a pair of spaced-apart rings each having a plurality of radially extending brushes of magnetically conductive material extending from a periphery surface. These brushes are adapted for contact with the interior surface of the pipe. A plurality of the support devices are mounted in spaced-apart relation on the periphery surface of the rings with the wheel of each support device being adapted for contact with the interior surface of a pipe during movement of the inspection tool through the pipe for inspection. The radially extending brushes are positioned on the periphery surface of the rings at locations between the locations of the support devices on the periphery surface.

BRIEF DESCRIPTION OF THE DRAWINGS

FIG. 4 is a front view of the magnetizer portion of an in-line pipe inspection tool showing the support device of FIGS. 2 and 3 mounted thereon;

FIG. 5 is a view of the inspection tool of FIG. 4 in cross-section;

DESCRIPTION OF THE PREFERRED EMBODIMENT

Figure 1:
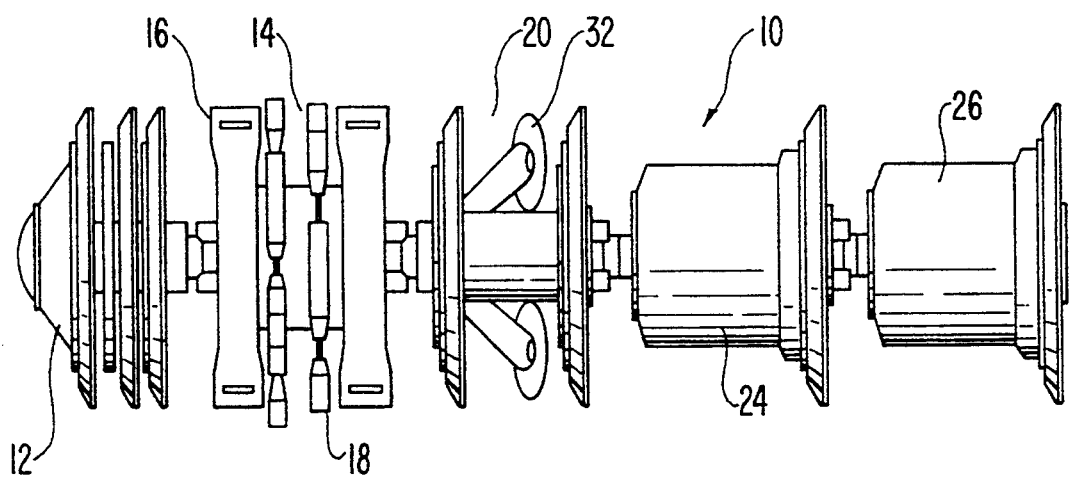
FIG. 1 is an elevational view in assembly of a conventional in-line pipe inspection tool with which the support device of the invention may be used.

With reference to the drawings, and for the present to FIG. 1 thereof, there is shown a typical in-line pipe inspection tool designated generally as 10. This tool is of the type adapted for longitudinal travel in the right to left direction as viewed in FIG. 1 through a pipeline to perform inspection for defects using magnetic flux leakage technology. The tool is moved through the pipeline by the product flow through the pipeline, which product may be for example oil.

The tool 10 as shown in FIG. 1, includes a plurality of drive cups 12 that form a positive seal on the internal surface of the pipe to allow the tool to be propelled through the pipe by the pipeline product. A magnetizing section 14 is located behind the drive cups and performs the actual pipeline inspection. The major components of this section are an electromagnet (not shown), steel brushes and transducers. The steel brushes are designated as 16 and the transducers are designated as 18. The electromagnet is battery-powered and provides the magnetic force which induces the magnetic flux field into the pipe wall. The steel brushes are provided as shown in FIG. 1 in two sets with one being the magnetic north and the other the south poles of the magnetic flux field. Constant contact is required between these two sets of steel brushes with the interior pipe wall to provide an uninterrupted magnetic flux field in the width of the pipe wall. As will be shown and described hereinafter, the support device of the invention finds utility in combination with these steel brushes of the magnetizer to provide for improved performance from the standpoint of properly supporting the tool relative to the internal surface of the pipe during travel through the pipe. The transducers are positioned to overlap the complete 360° inspection surface of the pipe wall. When a defect is present in the pipe wall, these transducers detect the corresponding leakage of the magnetic flux field and then transmit a signal indicating the presence of this defect to an electronic recording unit.

The tool 10 further includes a distance measuring section 20 having wheels 22 that measure the progress of the tool as it moves through the pipeline. This information may for example be recorded on magnetic tape. A recorder section 24 is provided to process the data detected by the transduce and recorded on magnetic tape. The recorder section also may house necessary electronic components, such as amplifiers and the like. A battery section 26 of the tool is used to house the batteries that supply the electrical current necessary to operate the magnetizer and recorder. This section includes a pressure proof compartment that protects the battery from the pipeline pressure and product.

Figure 2:
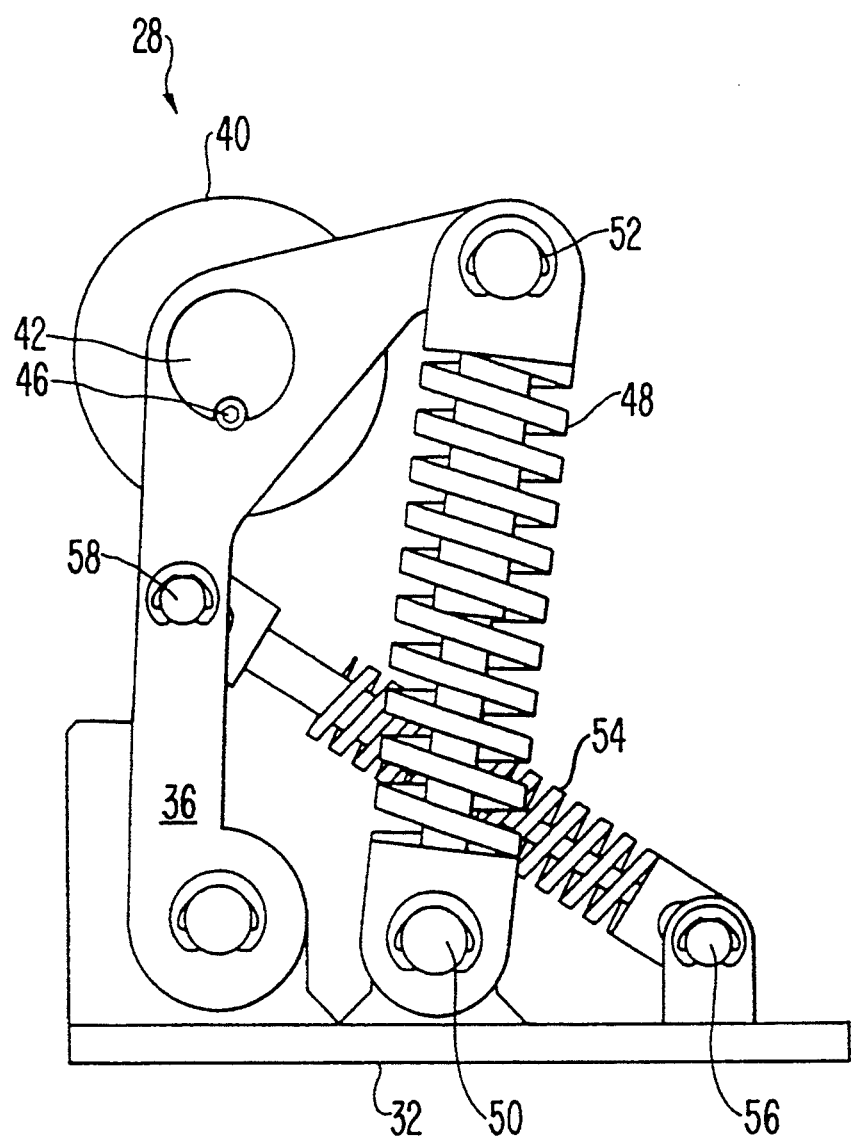
FIG. 2 is an elevational view of one embodiment of the support device of the invention.
Figure 3:
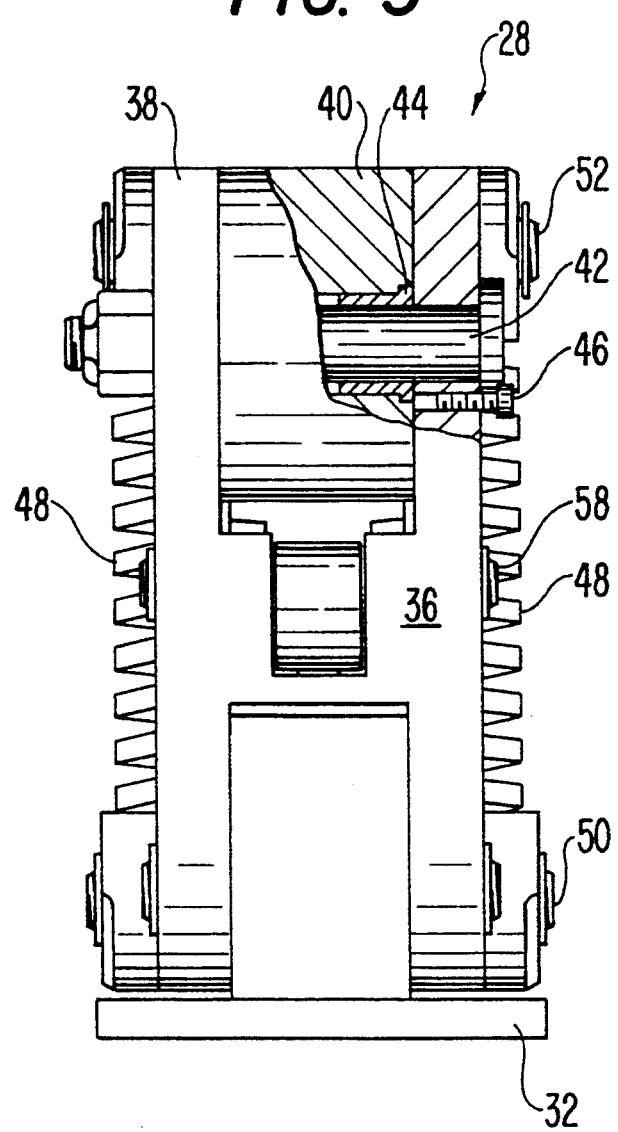
FIG. 3 is a front elevation view in partial section of the device of FIG. 2.

In accordance with an embodiment of the invention, the support device thereof is shown in detail in FIGS. 2 and 3 and is designated generally as 28. This support device 28 is mounted on a magnetic ring 30, as shown in FIG. 5, which is a component of a magnetizer section of an in-line inspection tool of the construction shown in FIG. 1.

The support device 28 includes a base plate 32 used to connect the device 28 to the ring 30 by bolts 34, as shown in FIG. 5.

A wheel-support 36 is connected to the base plate 32 and has an upper bifurcated portion 38 within which a wheel 40 is journaled for rotation on shaft 42 and bearings 44. The shaft 42 is secured by screw 46. A pair of springs 48 are parallel connected at one end to the base plate and at the other to wheel support 36 at pivotal connections 50 and 52, respectively. A second spring 54 is bias mounted between the pair of springs 48 and is connected at one end to the base plate and at the other end to the wheel support 36 at pivotal connections 56 and 58, respectively.

As shown in FIGS. 4 and 5, a plurality of the support devices 28 are mounted on the ring 30 in equi-spaced apart relation with pairs of steel brushes 60 being mounted on the ring between each support device 28.

With the ring 30 shown in FIGS. 4 and 5 and having mounted thereon the plurality of support devices 28 in accordance with the invention, as the inspection tool moves through the pipeline, the brushes 60 contact the interior surface of the pipeline to produce the magnetic flux field in the pipe wall. The wheels 40 of the support device 28 are also in contact with the interior surface of the pipeline during this operation to provide the required support for the inspection tool. In the presence of an increase in the inside diameter of the pipeline, such as encountered during the inspection of pipe of increased diameter, the wheel 40 will be moved toward the pipe wall by the force provided by springs 48. The biasing force of the spring 54 aids in recentralizing the magnetizing section 14 by providing a supplemental lifting force as the tool enters the larger diameter pipe. In this manner, the wheel force is sufficiently maintained to provide for effective inspection as the inspection tool moves through larger-diameter portions of the pipeline. Hence, the support device 28 provides sufficient force to properly support the inspection tool concentrically within the interior of the pipeline during longitudinal movement of the tool, even with pipe of increased diameter. This avoids the prior-art problem of deterioration of the steel brushes 60 as a result of supporting the inspection tool within the pipeline. In addition, this permits the device to be effectively used for inspection of pipe of various diameters by providing an uninterrupted magnetic flux field within the pipe wall. Specifically in this regard, the same device may be used to effectively inspect pipe of both 30 and 32 inch inside diameters.

Figure 6A:
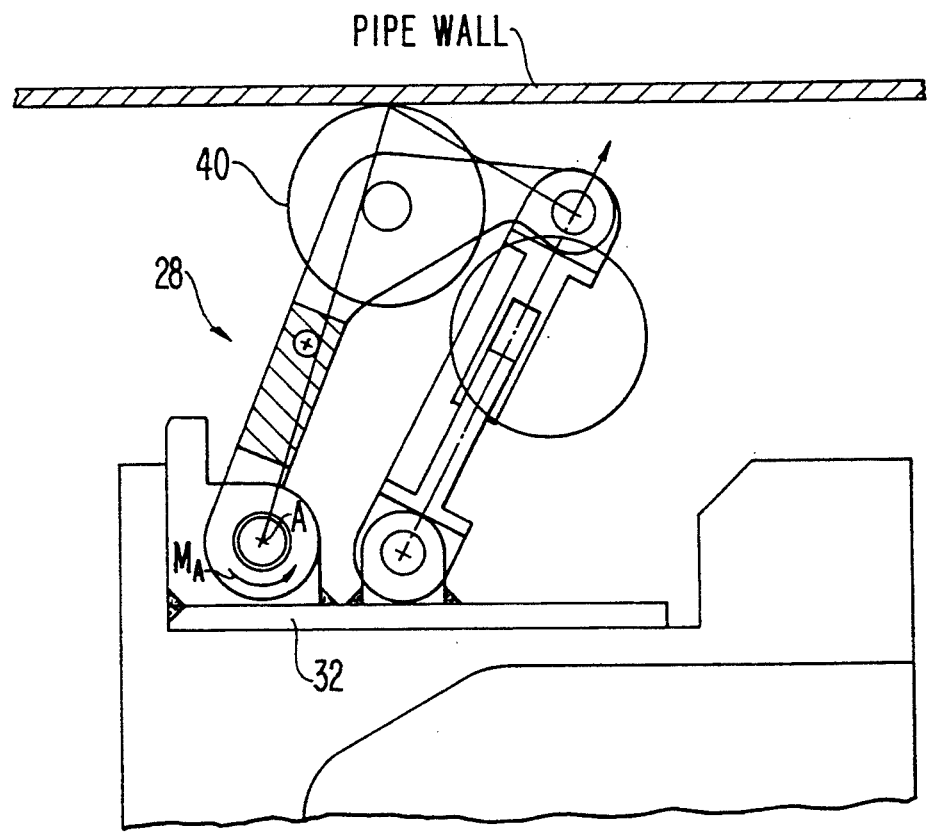
FIGS. 6A and B show a typical example of force and vector product calculations of an embodiment of the tool of the invention for inspection of pipe having a diameter of 32 inches.
Figure 6B:
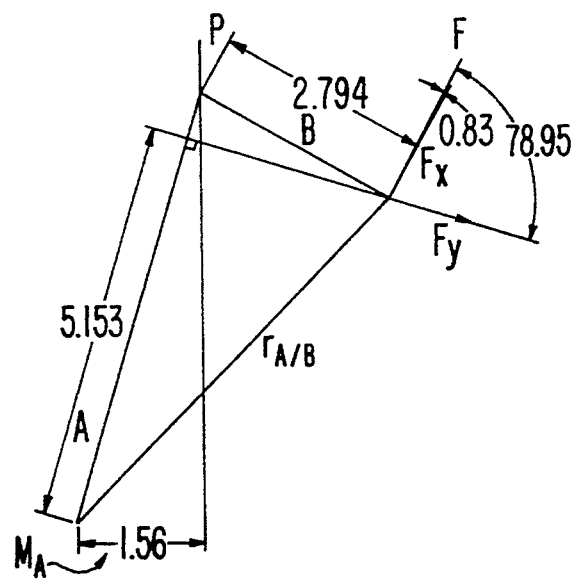

FIGS. 6A and B relate to the following specific example of force and vector product calculations for an embodiment of the support device of the invention relating to use in inspecting pipe having an inside diameter of 32 inches:

Spring Force = 1,078.2 lbs.

$P$ = Force of Wheel at Point of Contact with Pipe Wall
  = $M_A/d$ = 1947.3 lb.in/1.66 in
  = <u>1173.07 lbs.</u>

Moment M about A is the vector product:

$$M_A = r_{A/B} \times F$$

where
$F = F_x + F_y$
$F_x$ being the component of F normal to the moment arm B
$F_y$ being the component of F normal to the moment arm A
in this case, $F_y$ is a force opposing the counter-clockwise rotation about $M_A$.

$F$ = 1078.2 lbs (cos 0.83°) − 1078.2 lbs (cos 78.95°)
  = 1079.09 lbs − 206.65 lbs $M_A$ = $B(F_x) - A(F_y)$
  = 2.794 in (1078.09 lbs) − 5.153 in (206.65 lbs)
  = 3012.18 lb.in − 1064.87 lb.in
  = 1.947.3 lb.in The biasing spring 54 is not compressed during the inspection of 32 inch diameter pipe and therefore, the total force of wheel 40 at point of contact with the pipe wall is 1,173.07 pounds.

Figure 7A:
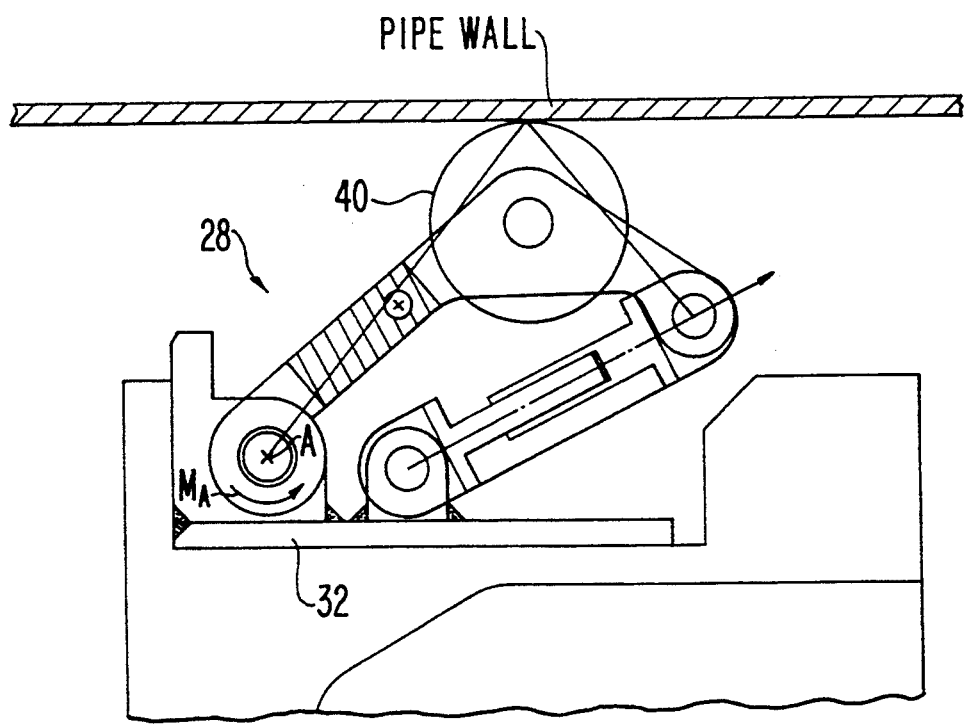
FIGS. 7A and B show a similar typical example of an embodiment for the inspection of pipe having a diameter of 30 inches.
Figure 7B:
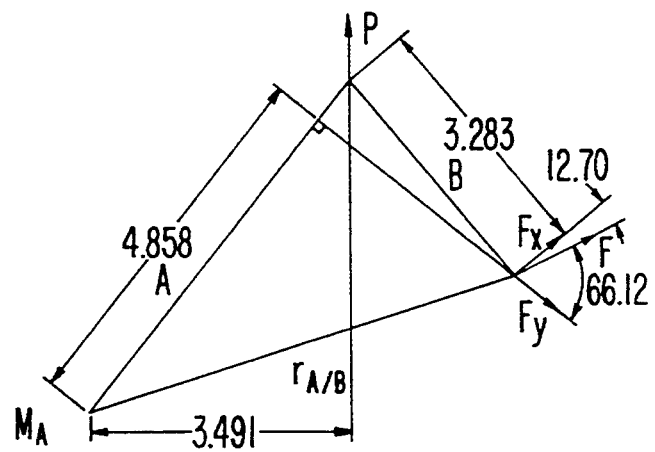

FIGS. 7A and B relate to the following specific example of force and vector product calculations for an embodiment of the support device of the invention relating to use in inspecting pipe having an inside diameter of 30 inches.

Spring Force = 2,386.6 lbs.

$P$ = Force of Wheel at Point of Contact with Pipe Wall
  = $M_A/d$ = 2949.8 lb.in/3.491 in
  = <u>845 lbs.</u>

Moment M about A is the vector product:

$$M_A = r_{A/B} \times F$$

where
$F = F_x + F_y$
$F_x$ being the component of F normal to the moment arm B
$F_y$ being the component of F normal to the moment arm A
in this case, $F_y$ is a force opposing the counterclockwise rotation about $M_A$.

$F$ = 2386.5 lbs (cos 12.7°) − 2386.5 lbs (cos 66.12°)
  = 2328.1 lbs − 966.1 lbs $M_A$ = $B(F_x) - A(F_y)$
  = 3.283 in (2328.1 lbs) − 4.858 in (966.1 lbs)
  = 7643.1 lb.in − 4693.3 lb.in
  = 2949.8 lb.in The resultant force of the springs 48 is 845 pounds, with the biasing spring 54 being compressed and providing an additional 250 pounds of force at wheel 40 point contact with the pipe wall. Therefore, the total force at point contact of wheel 40 with the pipe wall is 1,095 pounds.

In accordance with this specific example, when the tool passes from a 30-inch diameter pipe to a 32-inch diameter pipe, the biasing spring 54 extends to provide a supplemental force to that of the springs 48 to rapidly and effectively position the magnetizing section 14 within the pipe.

What is claimed:

1. A variable force support device for supporting an in-line pipe inspection tool during longitudinal travel of the tool through a pipe being inspected, said device comprising, rotating means for rotational contact with an interior surface of said pipe during travel of said tool through the pipe, a first spring means for applying force to said rotating means to normally urge said rotating means against said interior surface and adapted for compression in response to a compressive force transmitted thereto from said rotating means resulting from contact of said rotating means with said interior surface, a second spring for applying a supplemental biasing force to said rotating means with said supplemental biasing force increasing in relation to decreases in the force applied by said first spring means to minimize force changes between said rotating means and said interior surface.

2. The device of claim 1 further comprising, said rotating means being a wheel provided for rotation during longitudinal travel of the inspection tool through the pipe being inspected.

3. The device of claim 2 further comprising, said first spring means including a pair of coil springs.

4. The device of claim 3 further comprising, said pair of coil springs being parallel mounted on said support device at opposite ends of said wheel.

5. The device of claim 4 further comprising, said second spring being bias mounted on said support device relative to said pair of coil springs.

6. The device of claim 5 further comprising, said means connecting said support device to said inspection tool including a base plate, a wheel support connected to and extending from said base plate at one end and at an opposite end having a bifurcated portion within which said wheel is journaled for rotation, an end of each of said pair of coil springs being connected to said bifurcated portion and an opposite end thereof being connected to said base plate, an end of said second spring being connected to said base plate and an opposite end being connected to said wheel support at a location thereon between said wheel and said base plate.

7. The device of claim 6 further comprising, said inspection tool including a magnetizing portion that comprises a pair of spaced-apart rings each having a plurality of radially extending brushes of magnetically conductive material extending from a periphery surface and adapted for contact with the interior surface of the pipe and relation on the periphery surface with the wheel of each device adapted for contact with the interior surface of the pipe.

8. The device of claim 7 further comprising, said radially extending brushes being on said periphery surface at locations between said support devices.

* * * * *

UNITED STATES PATENT AND TRADEMARK OFFICE
CERTIFICATE OF CORRECTION

PATENT NO. : 5,359,939
DATED : November 1, 1994
INVENTOR(S) : Robert L. WATT

It is certified that error appears in the above-indentified patent and that said Letters Patent is hereby corrected as shown below:

Claim 7, column 6, line 62, before "relation" insert

--a plurality of said support devices mounted in spaced-apart--.

Signed and Sealed this

Twenty-first Day of February, 1995

Attest:

BRUCE LEHMAN

Attesting Officer

Commissioner of Patents and Trademarks